United States Patent
Truitt, III et al.

(10) Patent No.: US 11,213,566 B2
(45) Date of Patent: *Jan. 4, 2022

(54) ORAL CARE COMPOSITIONS AND METHODS

(75) Inventors: Edward R. Truitt, III, San Diego, CA (US); Benjamin Sullivan, San Diego, CA (US); Nicholas Tennison, University Place, WA (US)

(73) Assignee: LUBRIS LLC, Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/574,095

(22) PCT Filed: Jan. 19, 2011

(86) PCT No.: PCT/US2011/021669
§ 371 (c)(1),
(2), (4) Date: Sep. 18, 2012

(87) PCT Pub. No.: WO2011/091000
PCT Pub. Date: Jul. 28, 2011

(65) Prior Publication Data
US 2013/0039865 A1 Feb. 14, 2013

Related U.S. Application Data

(60) Provisional application No. 61/296,259, filed on Jan. 19, 2010.

(51) Int. Cl.
*A61K 38/17* (2006.01)

(52) U.S. Cl.
CPC .................. *A61K 38/1709* (2013.01)

(58) Field of Classification Search
None
See application file for complete search history.

(56) References Cited

U.S. PATENT DOCUMENTS

| | | |
|---|---|---|
| 5,326,558 A | 7/1994 | Turner et al. |
| 6,433,142 B1 | 8/2002 | Turner et al. |
| 6,743,774 B1 | 6/2004 | Jay |
| 6,960,562 B2 | 11/2005 | Jay |
| 7,030,223 B2 | 4/2006 | Turner et al. |
| 7,361,738 B2 | 4/2008 | Turner et al. |
| 2007/0191268 A1 | 8/2007 | Turner et al. |
| 2007/0275032 A1 | 11/2007 | Wimmer et al. |
| 2008/0139458 A1 | 6/2008 | Jay et al. |
| 2008/0177218 A1 | 7/2008 | McKay et al. |
| 2008/0292779 A1 | 11/2008 | Mercuri et al. |
| 2012/0134925 A1* | 5/2012 | Sullivan et al. ........... 424/9.1 |

FOREIGN PATENT DOCUMENTS

| | | |
|---|---|---|
| WO | WO2010135736 A2 | 11/2010 |
| WO | WO2011091000 A2 | 7/2011 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Canker sore information from Medline Plus (http://www.nlm.nih.gov/medlineplus/ency/article/000998.htm; downloaded Apr. 5, 2015).*
NCBI database information for human PRG4 (downloaded from https://www.ncbi.nlm.nih.gov/gene/10216#general-protein-info on Oct. 1, 2019) (Year: 2019).*
International Search Report for PCT/US2011/021669, dated Sep. 27, 2011 (3 pages).
Written Opinion for PCT/US2011/021669, dated Sep. 27, 2011 (4 pages).
Extended Supplementary European Search Report with Annex for European Patent App. No. 11 73 5084 dated Aug. 29, 2013, related to present application.
Sukumar et al., Hyaluronic Acid and Periodontitis, Jul. 2007; 50(4)pp. 225-228, Acta Medica, XP-002711447.
Ai et al., (2005), "Anti-Lubricin Monoclonal Antibodies Created Using Lubricin-knockout Mice Immunodetect Lubricin in Several Species and in Patients with Healthy and Diseased Joint," PLOS ONE, DOI:10.1371, p. 1-17.
Flannery et al., (1999), "Articular Cartilage Superficial Zone Protein (SZP) is Homologous to Megakaryocyte Stimulating Factor Precursor and is a Multifunctional Proteoglycan with Potential Growth-Promoting, Cytoprotective, and, and Lubricating Properties in Cartilage Metabolism," Biochem. Biophys. Res. Comm. 254:535-541.
Ikegawa et al., (2000), "Isolation, characterization and mapping of the mouse and human PRG4 (proteoglycan 4) genes," Cytogenet Cell Genet 90:291-297.
Jay et al., (2001), "Boundary lubrication by lubricin is mediated by O-linked β(1-3)Gal-GalNAc Oligosaccharides," *Glyconj. J.*, 18:807-815.
Rhee et al., (2005), "Consequences of Disease-causing Mutations on Lubricin Protein Synthesis, Secretion, and Post-translation Processing," *J. Biol. Chem.*, 280(35):31325-31332.

* cited by examiner

*Primary Examiner* — Brian Gangle
*Assistant Examiner* — Andrea K McCollum
(74) *Attorney, Agent, or Firm* — Goodwin Procter LLP

(57) ABSTRACT

Provided herein is a pharmaceutical or oral care product for treating or preventing oral diseases that is prepared with proteoglycan 4 (PRG4) as an active ingredient, the preparing method thereof and the use thereof in manufacturing medicaments or oral care products for treating or preventing oral diseases and maintenance of oral health. PRG4 may have efficacy in maintaining oral health and treating or preventing oral disease. This secreted glycoprotein, which is also called lubricin and superficial zone protein, is known to protect against frictional forces, cell adhesion and protein deposition.

17 Claims, No Drawings
Specification includes a Sequence Listing.

SEQUENCE LISTING

<160> NUMBER OF SEQ ID NOS: 4

<210> SEQ ID NO 1
<211> LENGTH: 1404
<212> TYPE: PRT
<213> ORGANISM: Homo sapiens

<400> SEQUENCE: 1

```
Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Val Glu Thr Lys Glu
        275                 280                 285

Thr Thr Thr Thr Asn Lys Gln Thr Ser Thr Asp Gly Lys Glu Lys Thr
    290                 295                 300
```

```
Thr Ser Ala Lys Glu Thr Gln Ser Ile Glu Lys Thr Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
            355                 360                 365

Thr Thr Ile Lys Ser Ala Pro Thr Thr Pro Lys Glu Pro Ala Pro Thr
            370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
                420                 425                 430

Lys Glu Pro Ala Pro Thr Thr Pro Lys Pro Ala Pro Thr Thr Pro
            435                 440                 445

Lys Glu Pro Ala Pro Thr Thr Pro Lys Glu Pro Thr Pro Thr Thr Pro
450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
                500                 505                 510

Glu Pro Ser Pro Thr Thr Pro Lys Glu Pro Ala Pro Thr Thr Thr Lys
                515                 520                 525

Ser Ala Pro Thr Thr Thr Lys Glu Pro Ala Pro Thr Thr Thr Lys Ser
530                 535                 540

Ala Pro Thr Thr Pro Lys Glu Pro Ser Pro Thr Thr Lys Glu Pro
545                 550                 555                 560

Ala Pro Thr Thr Pro Lys Glu Pro Ala Pro Thr Thr Pro Lys Lys Pro
                565                 570                 575

Ala Pro Thr Thr Pro Lys Glu Pro Ala Pro Thr Thr Pro Lys Glu Pro
                580                 585                 590

Ala Pro Thr Thr Thr Lys Lys Pro Ala Pro Thr Thr Pro Lys Glu Pro
                595                 600                 605

Ala Pro Thr Thr Pro Lys Glu Thr Ala Pro Thr Thr Pro Lys Lys Leu
                610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
                675                 680                 685

Ala Pro Thr Thr Pro Lys Glu Pro Ala Pro Thr Thr Pro Lys Glu Thr
                690                 695                 700

Ala Pro Thr Thr Pro Lys Gly Thr Ala Pro Thr Thr Leu Lys Glu Pro
705                 710                 715                 720
```

```
Ala Pro Thr Thr Pro Lys Lys Pro Ala Pro Lys Glu Leu Ala Pro Thr
            725                 730                 735

Thr Thr Lys Glu Pro Thr Ser Thr Thr Cys Asp Lys Pro Ala Pro Thr
            740                 745                 750

Thr Pro Lys Gly Thr Ala Pro Thr Thr Pro Lys Glu Pro Ala Pro Thr
            755                 760                 765

Thr Pro Lys Glu Pro Ala Pro Thr Thr Pro Lys Gly Thr Ala Pro Thr
            770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
            805                 810                 815

Lys Pro Ala Pro Thr Thr Pro Lys Glu Thr Ala Pro Thr Thr Pro Lys
            820                 825                 830

Glu Pro Ala Pro Thr Thr Pro Lys Lys Pro Ala Pro Thr Thr Pro Glu
            835                 840                 845

Thr Pro Pro Pro Thr Thr Ser Glu Val Ser Thr Pro Thr Thr Thr Lys
            850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
            885                 890                 895

Gly Val Pro Thr Thr Lys Thr Pro Ala Ala Thr Lys Pro Glu Met Thr
            900                 905                 910

Thr Thr Ala Lys Asp Lys Thr Thr Glu Arg Asp Leu Arg Thr Thr Pro
            915                 920                 925

Glu Thr Thr Thr Ala Ala Pro Lys Met Thr Lys Glu Thr Ala Thr Thr
            930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
            965                 970                 975

Lys Thr Thr Thr Leu Ala Pro Lys Val Thr Thr Thr Lys Lys Thr Ile
            980                 985                 990

Thr Thr Thr Glu Ile Met Asn Lys Pro Glu Glu Thr Ala Lys Pro Lys
            995                 1000                1005

Asp Arg Ala Thr Asn Ser Lys Ala Thr Thr Pro Lys Pro Gln Lys
            1010                1015                1020

Pro Thr Lys Ala Pro Lys Lys Pro Thr Ser Thr Lys Lys Pro Lys
            1025                1030                1035

Thr Met Pro Arg Val Arg Lys Pro Lys Thr Thr Pro Thr Pro Arg
            1040                1045                1050

Lys Met Thr Ser Thr Met Pro Glu Leu Asn Pro Thr Ser Arg Ile
            1055                1060                1065

Ala Glu Ala Met Leu Gln Thr Thr Thr Arg Pro Asn Gln Thr Pro
            1070                1075                1080

Asn Ser Lys Leu Val Glu Val Asn Pro Lys Ser Glu Asp Ala Gly
            1085                1090                1095

Gly Ala Glu Gly Glu Thr Pro His Met Leu Leu Arg Pro His Val
            1100                1105                1110

Phe Met Pro Glu Val Thr Pro Asp Met Asp Tyr Leu Pro Arg Val
            1115                1120                1125

Pro Asn Gln Gly Ile Ile Ile Asn Pro Met Leu Ser Asp Glu Thr
```

```
            1130                1135                1140

Asn Ile Cys Asn Gly Lys Pro Val Asp Gly Leu Thr Thr Leu Arg
    1145                1150                1155

Asn Gly Thr Leu Val Ala Phe Arg Gly His Tyr Phe Trp Met Leu
    1160                1165                1170

Ser Pro Phe Ser Pro Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 2
<211> LENGTH: 7
<212> TYPE: PRT
<213> ORGANISM: Homo sapiens

<400> SEQUENCE: 2

Lys Glu Pro Ala Pro Thr Thr
1               5

<210> SEQ ID NO 3
<211> LENGTH: 18
<212> TYPE: DNA
<213> ORGANISM: Homo sapiens

<400> SEQUENCE: 3
gatgcagggt accccaaa                                                   18

<210> SEQ ID NO 4
```

```
<211> LENGTH: 22
<212> TYPE: DNA
<213> ORGANISM: Homo sapiens

<400> SEQUENCE: 4
cagactttgg ataaggtctg cc                                              22
```

ORAL CARE COMPOSITIONS AND METHODS

CROSS-REFERENCE TO RELATED APPLICATION

This application is the national stage of International (PCT) Patent Application Serial No. PCT/US2011/021669, filed Jan. 19, 2011, which claims the benefit of U.S. Provisional Application No. 61/296,259, filed Jan. 19, 2010, the entire contents of each of which are hereby incorporated by reference in their entireties.

FIELD OF THE INVENTION

Provided herein are oral care compositions and methods utilizing PRG4 to improve oral health.

BACKGROUND OF THE INVENTION

To date, a wide variety of oral care products are available which, over the short term, aid the maintenance of good oral hygiene by delivering various oral care substances or actives to the soft and hard tissues of the oral cavity. The most frequently used oral hygiene treatments are those administered by the consumer themselves and it is usual that these are practiced, in the Western world, either once or twice a day.

SUMMARY OF THE INVENTION

Provided herein is a pharmaceutical or oral care product for treating or preventing oral diseases that is prepared with proteoglycan 4 (PRG4) as an active ingredient, the method for preparation thereof, and the oral care products for use in the treatment or prevention of oral diseases and maintenance of oral health. In certain embodiments, PRG4 provided herein has efficacy in maintaining oral health and treating or preventing oral disease. In some embodiments, PRG4, which is a secreted glycoprotein (also known as lubricin and superficial zone protein) protects against frictional forces, cell adhesion, and protein deposition.

Provided in certain embodiments herein, are compositions and methods for maintaining oral health and treating oral disease, or symptoms associated therewith, in an individual in need thereof comprising topically administering to the oral cavity of the individual a oral care composition comprising a effective amount of PRG4 protein. Also provided in some embodiments herein are oral care compositions comprising PRG4 protein in combination with an oral care active.

In certain embodiments, provided herein is an oral care composition suitable for application to an oral surface comprising an effective concentration of a PRG4 polypeptide or a functional fragment thereof suspended in an orally acceptable solution.

In some embodiments, a composition provided herein further comprises an oral care active. In some embodiments, the oral care active is selected from the group consisting of teeth color modifying substances, anti-tartar agents, anti-plaque agents, fluoride ion sources, anti-microbial agents, peroxides, polyphosphates, xylitol, triclosan, stannous fluoride, soluble zinc salts, potassium nitrate, and mixtures thereof. In some embodiments, the composition comprises from about 0.01% to about 20%, by weight, of an oral care active. In some embodiments, the composition comprises from about 0.1% to about 20%, about 0.5% to about 20%, about 1% to about 20%, about 5% to about 20%, about 10% to about 20%, about 15% to about 20%, about 0.01% to about 15%, about 0.01% to about 10%, about 0.01% to about 5%, about 0.01% to about 1%, about 0.01% to about 0.5%, about 0.01% to about 0.1%, about 0.01% to about 0.05%, about 1% to about 15%, about 5% to about 10%, by weight, of an oral care active.

In some embodiments, a composition provided herein comprises one or more orally acceptable agents selected from the group consisting of an orally acceptable demulcent, an orally acceptable excipient, an orally acceptable astringent, an orally acceptable vasoconstrictor, and an orally acceptable emollient.

In some embodiments, the effective concentration of a PRG4 polypeptide or a functional fragment thereof is between 10 µg/mL and 10,000 µg/mL. In some embodiments, the effective concentration of a PRG4 polypeptide or a functional fragment thereof is between 20 µg/mL and 9000 µg/mL; 30 µg/mL and 8000 µg/mL; 40 µg/mL and 7000 µg/mL; 60 µg/mL and 6000 µg/mL; 70 µg/mL and 5000 µg/mL; 80 µg/mL and 4000 µg/mL; 90 µg/mL and 3000 µg/mL; 100 µg/mL and 2000 µg/mL; 200 µg/mL and 1000 µg/mL; 300 µg/mL and 900 µg/mL; 400 µg/mL and 800 µg/mL; 500 µg/mL and 700 µg/mL; or 50 µg/mL and 500 µg/mL. In certain embodiments, the pharmaceutically effective concentration of PRG4 protein is in a range of 10-10,000 µg/mL, preferably 50-5,000 µg/mL, and more preferably 100-300 µg/mL. In certain embodiments, the oral care composition comprises the PRG4 in the effective concentration of 50-500 µg/mL.

In some embodiments, the oral care composition provided herein further comprises one or more additional agents selected from the group consisting of sodium hyaluronate, surface active phospholipids, and electrolytes in an orally acceptable carrier for topical administration. In some embodiments, a composition provided herein further comprises an effective concentration of sodium hyaluronate or hyaluronic acid. In certain embodiments, the effective concentration of sodium hyaluronate or hyaluronic acid is between 10 µg/mL and 100,000 µg/mL. In some embodiments, the effective concentration of sodium hyaluronate or hyaluronic acid is between 500 µg/mL and 5,000 µg/mL. In certain embodiments, the oral care composition comprises sodium hyaluronate or hyaluronic acid in the effective concentration of 10-100,000 µg/mL. In certain embodiments, the oral care composition comprises sodium hyaluronate or hyaluronic acid in the effective concentration of 500-5,000 µg/mL.

In certain embodiments, the oral care composition further comprises a effective concentration of surface active phospholipid selected from the group consisting of L-α-dipalmitoylphosphatidylcholine, phosphatidylcholine, phosphatidylethanolamine and sphingomyelin. In certain embodiments, a composition provided herein further comprises an effective concentration of a surface active phospholipid selected from the group consisting of L-α-dipalmitoylphosphatidylcholine, phosphatidylcholine, phosphatidylethanolamine, and sphingomyelin. In one embodiment, the oral care composition further comprises the surface active phospholipid in the effective concentration of 10-10,000 µg/mL. In another embodiment, the effective concentration of the surface active phospholipid is between 10 µg/mL and 10,000 µg/mL.

In certain embodiments, an orally acceptable solution provided herein comprises at least three different electrolytes selected from the group consisting of sodium phosphate, sodium chloride, potassium chloride, sodium bicarbonate, potassium bicarbonate, calcium chloride, magnesium chloride, sodium acetate, sodium citrate, hydrochloric acid, and sodium hydroxide.

In certain embodiments, the PRG4 polypeptide or the functional fragment thereof has an average molar mass of between 50 kDa and 400 kDa.

In certain embodiments, the PRG4 polypeptide or the functional fragment thereof comprises a lubricating fragment, multimer or a homolog thereof.

In certain embodiments, the PRG4 polypeptide or the functional fragment thereof is a recombinant PRG4 protein or a functional fragment thereof.

In certain embodiments, the PRG4 polypeptide or the functional fragment thereof is an isolated wild type PRG4 protein.

In certain embodiments, a composition provided herein comprises water in silicone emulsion and wherein the emulsion comprises from about 5% to about 95%, by weight, of the composition.

In certain embodiments, a composition provided herein comprises an internal aqueous phase comprising a rheology modifier selected from the group consisting of a cellulose polymer, xanthan gum, carbomer, inorganic clay polymer, polycarboxylate, EO/PO block copolymer (poloxamer), thickening silica, and mixtures thereof.

In certain embodiments, provided herein is a method for treating periodontal disease in an individual comprising administering to an oral cavity of said individual a therapeutically effective amount of an oral care composition suitable for application to an oral surface comprising an effective concentration of a PRG4 polypeptide or a functional fragment thereof suspended in an orally acceptable solution.

In certain embodiments, provided herein is a method for treating dental caries in an individual comprising administering to an oral cavity or teeth of said individual a therapeutically effective amount of an oral care composition suitable for application to an oral surface comprising an effective concentration of a PRG4 polypeptide or a functional fragment thereof suspended in an orally acceptable solution.

In certain embodiments, provided herein is a method for modifying teeth color in an individual comprising administering to an oral cavity or teeth of said individual a therapeutically effective amount of an oral care composition suitable for application to an oral surface comprising an effective concentration of a PRG4 polypeptide or a functional fragment thereof suspended in an orally acceptable solution.

In certain embodiments, provided herein is a method for replenishing the pellicle layer in an individual comprising administering to an oral cavity or teeth of said individual a therapeutically effective amount of an oral care composition suitable for application to an oral surface comprising an effective concentration of a PRG4 polypeptide or a functional fragment thereof suspended in an orally acceptable solution.

In certain embodiments, provided herein is a method for treating periodontal disease in an individual comprising attaching a boundary lubricant molecule to the surface of a dental device in the individual. In some embodiments, the dental device is selected from the group consisting of braces, retainers, mandibular advancement devices, mouth guards, and mouthpieces. In some embodiments, the boundary lubricant molecule is a PRG4 polypeptide or a functional fragment thereof. In some embodiments, the boundary lubricant molecule is a hyaluronic acid. In some embodiments, the boundary lubricant molecule is a homobifunctional linker molecule. In some embodiments, the boundary lubricant molecule is a heterobifunctional linker molecule.

In some embodiments, provided herein is a method of attaching the boundary lubricant molecule comprises adsorption onto the prophylactic surface.

DETAILED DESCRIPTION OF THE INVENTION

Many of the processes that lead to a deterioration in the tissues of the oral cavity are on-going and, as such, can only be effectively treated, either prophylactically or therapeutically, by continuous attention, which is impractical, or by the use of long lasting treatments. To date, conventional product forms do not typically provide long lasting, prolonged or sustained therapeutic, prophylactic and/or cosmetic treatment benefits. Instead, the preparations take effect only for the relatively short period of time during which the teeth are being cleaned or the mouth is being rinsed. After product use, the active level on the hard and soft oral tissues diminishes rapidly. It would therefore be desirable to have an oral care product comprising one or more active substances which are substantive within the oral cavity and wherein the oral care product has a pleasant mouth feel such that its aesthetics are acceptable for long term use. It is also desirable to have a substantive oral care product wherein the active substances are released over a sustained period of time and thus able to provide a long lasting benefit.

Proteoglycan 4 (PRG4) and Boundary Lubrication

The proteoglycan 4 (prg4) gene encodes for highly glycosylated proteins termed megakaryocyte stimulating factor (MSF), lubricin, and superficial zone protein (SZP). Lubricin was first isolated from synovial fluid and demonstrated lubricating ability in vitro similar to synovial fluid at a cartilage-glass interface. Lubricin was later identified as a product of synovial fibroblasts and also shown to possess boundary lubricating ability at a latex-glass interface. O-linked β(1-3)Gal-GalNAc oligosaccharides within a large mucin like domain of 940 amino acids, encoded for by exon 6, were subsequently shown to mediate, in part, this boundary lubricating ability. SZP was first localized at the surface of explant cartilage from the superficial zone and isolated from conditioned medium. SZP also demonstrated lubricating ability at a cartilage-glass interface. These molecules, MSF, lubricin, and SZP, are collectively referred to as PRG4. PRG4 was also shown to be present at the surface of synovium, tendon, and meniscus. In addition, PRG4 has been shown to contribute, both at physiological and pathophysiological concentrations, to the boundary lubrication of apposing articular cartilage surfaces.

The functional importance of prg4 was shown by mutations that cause the camptodactyly-arthropathy-coxa vara-pericarditis (CACP) disease syndrome in humans. CACP is manifest by camptodactyly, noninflammatory arthropathy, and hypertrophic synovitis, with coxa vara deformity, pericarditis, and pleural effusion. Also, in PRG4-null mice, cartilage deterioration and subsequent joint failure were observed. Therefore, PRG4 expression is a necessary component of healthy synovial joints.

PRG4 is a member of the mucin family, which are generally abundant on epithelial linings and provide many functions, including lubrication and protection from invading microorganisms. The functional properties of mucins are generally determined by specialized glycosylation patterns and their ability to form multimers through intermolecular disulfide bonds, both of which are altered in chronic diseases (e.g., cystic fibrosis, asthma). Biochemical characterization of PRG4 isolated from synovial fluid showed molecular heterogeneity in O-glycosylation, which appears to mediate lubricating properties. Recent preliminary data on PRG4 from bovine synovial fluid has revealed the presence of disulfide-bonded dimers, in addition to the monomeric forms, predicted from the conserved cysteine-rich domains at both N- and C-terminals, along with an unpaired cysteine at the C-terminal.

The accumulation of PRG4 within synovial fluid and at the articular surface, are likely key functional determinants of PRG4's boundary lubricating ability. Recently, it was demonstrated that a significant, threefold secretion of PRG4 resulted from the dynamic shear loading of cultured chondrocytes, as compared to free-swelling or statically compressed cultures. This PRG4 synthesis and secretion by chondrocytes could significantly contribute to the concentration of PRG4 within synovial fluid, in both homeostatic and pathological conditions where physiological regulators are present. Although the amount of PRG4 bound to the surface does not appear to correlate with secretion rates, previous studies suggest surface bound PRG4 can exchange with endogenous PRG4 in synovial fluid, especially under the influence of mechanical perturbation. Clarification of the spatial and temporal aspects of PRG4 metabolism within the joint, particularly at the articular surface, would further the understanding of PRG4's contribution to the low-friction properties of articular cartilage, and possibly lead to treatments to prevent loss of this function. More remains to be determined about the processing, and the potentially additional or alternative functions of various PRG4 molecules of different molecular weight. Finally, the combination of chemical and mechanical factors to stimulate PRG4 expression in chondrocytes near the articular surface may be useful for creating tissue engineered cartilage from isolated subpopulations with a surface that is bioactive and functional in lubrication.

In boundary lubrication, load is supported by surface-to-surface contact, and the associated frictional properties are determined by lubricant surface molecules. This mode has been proposed to be important because the opposing cartilage layers make contact over ~10% of the total area, and this may be where most of the friction occurs. Furthermore, with increasing loading time and dissipation of hydrostatic pressure, lubricant-coated surfaces bear an increasingly higher portion of the load relative to pressurized fluid, and consequently, this mode can become increasingly dominant. Boundary lubrication, in essence, mitigates stick-slip, and is therefore manifest as decreased resistance both to steady motion and the start-up of motion. The latter situation is relevant to load bearing articulating surfaces after prolonged compressive loading (e.g., sitting or standing in vivo). Typical wear patterns of cartilage surfaces also suggest that boundary lubrication of articular cartilage is critical to the protection and maintenance of the articular surface structure.

The relevant extent to which fluid pressure/film versus boundary lubrication occurs classically depends on a number of factors. When lubricant film can flow between the conforming sliding surfaces, which can deform elastically, elastohydrodynamic lubrication occurs. Pressure, surface roughness, and relative sliding velocity determine when full fluid lubrication begins to break down and the lubrication enters new regimes. As velocity decreases further, lubricant films adherent to the articulating surfaces begin to contribute and a mixed regime of lubrication occurs. If the velocity decreases even further and only an ultra-thin lubricant layer composed of a few molecules remain, boundary lubrication occurs. A boundary mode of lubrication is therefore indicated by a friction coefficient (ratio of the measured frictional force between 2 contacting surfaces in relative motion to the applied normal force) during steady sliding being invariant with factors that influence formation of a fluid film, such as relative sliding velocity and axial load. For articular cartilage, it has been concluded boundary lubrication is certain to occur, although complemented by fluid pressurization and other mechanisms.

Provided herein are compositions and methods comprising providing PRG4 to improve oral health. Without wishing to be bound by any particular theory it is believed that PRG4 plays a critical role in oral health as a component of saliva and a component of the pellicle layer by providing lubricating and anti-adhesive benefits. The replenishment of PRG4 by itself or in combination with an oral care active will help to both prevent build up of plaque and provide sustained release and localization of the oral care active.

Provided herein is a substantive coating for the oral cavity which has acceptable mouth feel properties and which can prophylactically or therapeutically treat the surfaces of the oral cavity including by sustained release of an oral care active.

Oral Care Actives

In certain embodiments, oral care compositions or substances provided herein may include many of the actives previously discussed in the art. The following is a non-limiting list of oral care actives that may be used in the present embodiments:

Teeth Color Modifying Substances

In some embodiments, provided herein are oral actives comprising teeth color modifying substances. Teeth color modifying substances may be considered among the oral care actives useful in the present embodiments. These substances are suitable for modifying the color of the teeth to satisfy the consumer. These substances could be particles that when applied on the tooth surface modify that surface in terms of absorption and, or reflection of light. Such particles provide an appearance benefit when a file containing such particles is applied over the surfaces of a tooth or teeth. This benefit may last to the point wherein the film has eroded, or been removed, presenting for example a mottled or uniform looking tooth surface.

In one aspect, particles most useful in the present embodiments include pigments and colorants routinely used in the cosmetic arts. There are no specific limitations as to the pigment and, or colourant used in compositions provided herein other than the limitation of the effect it has on the light source upon the teeth surfaces. In some embodiments, pigments and colourants include inorganic white pigments, inorganic colored pigments, pearling agents, filler powders and the like; see Japanese Published Patent Application Kokai No 9 [1997]-100215, published Apr. 15, 1997, incorporated herein by reference. In some embodiments, pigments and colourants provided herein are selected from the group consisting of talc, mica, magnesium carbonate, calcium carbonate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. In a preferred embodiment, provided herein are those selected from the group consisting of titanium dioxide, bismuth oxychloride, zinc oxide and mixtures thereof. In some embodiments, pigments that are generally recognised as safe, and are listed in the CTFA Cosmetic Ingredient Handbook, 3.sup.rd Edition, Cosmetic and Fragrances Association Inc., Washington D.C. (1982), are incorporated herein by reference.

In certain embodiments, the pigments provided herein are used as opacifiers and colourants. In some embodiments, these pigments can be used as treated particles, or as the raw pigments themselves. In some embodiments, pigment levels are selected for the particular impact that is desirable by the consumer. In some embodiments, for teeth that are particularly dark or stained provided herein are pigments in sufficient amount to lighten the teeth. In some embodiments, where individual teeth or spots on the teeth are lighter than other teeth, pigments to darken the teeth may be useful. In some embodiments, the levels of pigments and colourants provided herein are in the range of about 0.05% to about 20%, about 0.05% to about 15%, about 0.1% to about 15%, preferably from about 0.1% to about 15% and most preferably from about 0.25% to about 10%, by weight, of the composition. In some embodiments, it is highly preferred that when a composition for use herein comprises a pigment it additionally comprises a further oral care active.

In certain embodiments, compositions for use herein may comprise materials that remove or bleach intrinsic or extrinsic stains on or in tooth surfaces. In some embodiments, such substances are selected from the group consisting of the peroxides, metal chlorites, perborates, percarbonates, peroxyacids, persulphates, and combinations thereof. In some embodiments, suitable peroxide compounds provided herein include hydrogen peroxide, urea peroxide, calcium peroxide, carbamide peroxide and mixtures thereof. Most preferred is carbamide peroxide. In some embodiments, suitable metal chlorites include calcium chlorite, barium chlorite, magnesium chlorite, lithium chlorite, sodium chlorite and potassium chlorite. In some embodiments, provided herein are additional bleaching substances, which may be hypochlorite, or chlorine dioxide. In one embodiment, a preferred chlorite is sodium chlorite. In one embodiments, a preferred percarbonate is sodium percarbonate. In one embodiment, preferred persulphates are oxones. The level of these substances is dependent on the available oxygen or chlorine respectively that the molecule is capable of providing to bleach the stain. In some embodiments, this level is used in compositions provided herein at levels from about 0.1% to about 35%, preferably from about 1% to about 25%, or most preferably from about 5% to about 10% of the composition.

Anti-Tartar Agents

Provided herein are anti-tartar agents known for use in dental care products include phosphate. In some embodiments, phosphates include pyrophosphates, polyphosphates, polyphosphonates and mixtures thereof. Pyrophosphates are among the best known for use in dental care products but polyphosphates are also considered to be highly useful in the compositions provided herein. In some embodiments, the pyrophosphate salts useful in the present compositions include the dialkali metal pyrophosphate salts, tetra-alkali metal pyrophosphate salts and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) and mixtures thereof, in their unhydrated as well as hydrated forms are the preferred species. While any of the above mentioned pyrophosphate salts may be used, tetrasodium pyrophosphate salt is preferred. In some embodiments, sodium polyphosphate and triethanolamine polyphosphates are preferred.

The pyrophosphate salts are described in more detail in Kirk and Othmer, Encyclopedia of Chemical Technology, $3^{rd}$ Edition, Volume 17, Wiley Interscience Publishers (1982). In some embodiments, additional anticalculus agents include pyrophosphates or polyphosphates disclosed in U.S. Pat. No. 4,590,066 issued to Parran and Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict and Sunberg on Apr. 28, 1987; polyepoxysuccinates such as those disclosed in U.S. Pat. No. 4,846,650 issued to Bendict, Bush and Sunberg on Jul. 11, 1989; ethylenediaminetetraacetic acid as disclosed in British Patent No 490,384 date Feb. 15, 1937; nitrilotriacetic acid and related compounds as disclosed in U.S. Pat. No. 3,678,154 issued to Widder and Briner on Jul. 18, 1972; polyphosphonates as disclosed in U.S. Pat. No. 3,737,533 issued to Francis on Jun. 5, 1973; U.S. Pat. No. 3,988,443 issued to Ploger, Schmidt-Dunker and Gloxhuber on Oct. 26, 1976 or U.S. Pat. No. 4,877,603 issed to Degenhardt and Kozikowski on Oct. 31, 1989. In some embodiments, anticalculus phosphates include potassium and sodium pyrophosphates; sodium tripolyphosphate; diphosphonates such as ethane-1-hydroxy-1,1-diphosphonate, 1-azacycloheptane-1, 1-diphosphonate, and linear alkyl disphosphonates; linear carboxylic acids; and sodium zinc citrate and other soluble zinc salts.

In certain embodiments, provided herein are polyphosphates. In some embodiments, polyphosphates preferred are those having a chain length of three or more, especially those with a chain length of around four or more phosphate molecules including tetrapolyphosphate or hexametaphosphate, among others. Polyphosphates larger than tetrapolyphosphate usually occur as amorphous glassy materials. In a preferred embodiment, the linear "glassy" polyphosphates has the formula: $XO(XPO_3)_nX$ wherein X is sodium, potassium, or hydrogen and n averages from about 6 to about 125. In a preferred embodiment, provided herein is a particulate sodium polyphosphate with an average chain length of from about 10 to about 30, from about 10 to about 25, from about 15 to about 30, preferably from about 15 to 25, more preferably from about 21 to about 23. Such polyphosphates are manufactured by FMC Corporation and are commercially available under the trade names SODA-PHOS for sodium hexametaphosphate granular (n.apprxeq.6), HEXAPHOS for sodium hexametaphosphate plates (n.apprxeq.13), and GLASS H for sodium hexametaphosphate long chain powder (n.apprxeq.21), all trademarks owned by ICL Performance Products of St. Louis, Mo. HEXAPHOS and GLASS H are preferred with GLASS H being the most preferred polyphosphate. In some embodiments, these polyphosphates may be used alone or in a combination thereof.

In some embodiments, agents that may be used in place of, or in combination with, the pyrophosphate salt include such known materials as synthetic anionic polymers including polyacrylates and copolymers of maleic anhydride or acid and methyl vinyl ether (e.g., the series of copolymers of monoalkyl esters of poly (methyl vinyl ether/maleic acid) with varying ester groups, supplied as clear, viscous solutions and available under the trade name GANTREZ owned by ISP Investments Inc. of Wilmington, Del.), as described, for example in U.S. Pat. No. 4,627,977 to Gaffer et al; as well as e.g., polyamino propane sulphonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids) and mixtures thereof.

Anti-Plaque Agents

In certain embodiments, provided herein are anti-plaque agents. Anti-plaque agents are any substances which inhibit the accumulation of bacterial deposits on the surfaces of the oral cavity. Examples include xylitol and other anti-microbial agents.

Fluoride Ion Source

In certain embodiments, provided herein are fluoride ion. In some embodiments, fluoride ion sources are provided herein for use in oral care compositions as anticaries agents. Fluoride ions are contained in a number of oral care compositions for this purpose, particularly toothpastes. Patents disclosing such toothpastes include U.S. Pat. No. 3,538,230, Nov. 3, 1970 issued to Pader et al; U.S. Pat. No. 3,689,637, September 5.sup.th, 1972 to Pader; U.S. Pat. No. 3,711,604, Jan. 16, 1973 to Colodney et al; U.S. Pat. No. 3,911,104 Oct. 7, 1975 to Harrison; U.S. Pat. No. 3,935,306, Jan. 26, 1976 to Roberts et al; and U.S. Pat. No. 4,040,858 Aug. 9, 1977 to Wasson.

Application of fluoride ions to dental enamel serves to protect teeth against decay. In some embodiments, a wide variety of fluoride ion yielding materials can be employed as sources of soluble fluoride in the present compositions. Examples of suitable fluoride ion yielding materials are found in U.S. Pat. No. 3,535,421, Oct. 20, 1970 issued to Briner et al and U.S. Pat. No. 3,678,154 Jul. 18, 1972 issued to Widder et al. In some embodiments, preferred fluoride ion sources for use herein include sodium fluoride, potassium fluoride, stannous fluoride, ammonium fluoride and mixtures thereof. In one embodiment, sodium fluoride is particularly preferred. In some embodiments, a present composition provides from about 50 ppm to about 10,000 ppm, from about 50 ppm to about 9,000 ppm, from about 100 ppm to about 9,000 ppm, from about 50 ppm to about 8,000 ppm, from about 100 ppm to about 8,000 ppm, from about 50 ppm to about 7,000 ppm, from about 100 ppm to about 7,000 ppm, from about 50 ppm to about 6,000 ppm, from about 100 ppm to about 6,000 ppm, from about 50 ppm to about 5,000 ppm, from about 100 ppm to about 5,000 ppm, from about 50 ppm to about 4,000 ppm, from about 100 ppm to about 4,000 ppm, from about 50 ppm to about 3,000 ppm, or more preferably from about 100 ppm to about 3000 ppm of fluoride ions in the compositions that contact dental surfaces when used with the delivery system provided herein.

Anti Microbial Agents

In some embodiments, antimicrobial agents can also be present in the oral care compositions or substances provided herein. Such agents may include, but are not limited to, 5-chloro-2-(2,4-dichlorophenoxy)-phenol, commonly referred to as triclosan, and described in the Merck Index, 11.sup.th Edition, (1989), pp 1529 (entry no 9573) in U.S. Pat. No. 3,506,720, and in European Patent Application No 0,251,591 of Beecham Group, Plc, published January 7.sup.th, 1988; phthalic acid and its slats including, but not limited to those disclosed in U.S. Pat. No. 4,994,262 published February 19.sup.th, 1991, preferably magnesium mono-potassium phthalate, chlorhexidine (Merck Index, no 2090); alexidine (Merck Index, no 222); hexetidine (Merck Index, no 4624); sanguinarine (Merck Index, no 8320); benzalkonium chloride (Merck Index, no 1066); salicylanilide (Merck Index, no 8299); domiphen bromide (Merck Index, no 3411); cetylpyridinium chloride (CPC) (Merck Index, no 2024); tetradecylpyridinium chloride (TPC); N-tetradecyl-4-ethylpyridinium chloride (TDEPC); octenifine; delmopinol; octapinol; and other piperidine derivatives; nicin preparations; zinc/stannous ion agents; antibiotics such as augmentin, amoxicilline, tetracycline, doxycycline, minocycline, and metronidazole; and analogues and salts of the above; essential oils including thymol, geraniol, carvacrol, citral, hinokitiol, eucalyptol, catechol (particularly 4-allyl catechol) and mixtures thereof; methyl salicyclate; hydrogen peroxide; metal salts of chlorite and mixtures of all of the above.

Nutrients

In some embodiments, nutrients may improve the condition of the oral cavity and can be include in the oral care compositions or substances provided herein. Nutrients include minerals, vitamins, oral nutritional supplements, enteral nutritional supplements, herbal supplements, natural extracts and mixtures thereof.

In some embodiments, minerals that can be included with the compositions provided herein include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., ©1997, pp. 10-17.

In some embodiments, vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St. Louis, Mo., ©1997, pp 3-10.

In some embodiments, provided herein are oral nutritional supplements. Oral nutritional supplements include amino acids, lipotropics, fish oil, coenzyme Q10, and mixtures thereof, as disclosed in Drug Facts and Comparisons (loose leaf drug information service), Wolters Kluer Company, St Louis, Mo., ©1997, pp. 54-54e. Amino acids include, but are not limited to L-tryptophane, L-lysine, methionine, threonine, levocarnitine or L-carnitine and mixtures thereof. Lipotropics include, but are not limited to choline, inositol, betaine, linoleic acid, linolenic acid and mixtures thereof. Fish oil contains large amounts of Omega-3 (N-3) polyunsaturated fatty acids, eicosapentaenoic acid and docosahexaenoic acid.

In some embodiments, provided herein are entenal nutritional supplements. Entenal nutritional supplements include, but are not limited to, protein products, glucose polymers, corn oil, safflower oil, medium chain triglycerides as disclosed in Drug Facts and Comparisons (loose leaf drug information service), Wolters Kluer Company, St. Louis, Mo., ©1997, pp. 55-57.

Antioxidants

In certain embodiments, antioxidants are useful in compositions provided herein. Antioxidants are disclosed in texts such as Cadenas and Packer, The Handbook of Antioxidants, ©1996 by Marcel Dekker, Inc. In certain embodiments, antioxidants that may be included in the oral care compositions provided herein include, but are not limited to, Vitamin E, ascorbic acid, Uric acid, carotenoids, Vitamin A, flavenoids and polyphenols, herbal antioxidants, melatonin, aminoindoles, lipoic acids and mixtures thereof.

H-2 Antagonists

In certain embodiments, Histamine-2 (H-2) receptor antagonist compounds (H-2 antagonists) may be used in the oral care compositions provided herein. As used herein, selective H-2 antagonists are compounds that block H-2 receptors, but do not have meaningful activity in blocking histamine-1 (H-1) receptors. Selective H-2 antagonists stimulate the contraction of smooth muscle from various organs, such as the gut and bronchi; this effect can be suppressed by low concentrations of mepyramine—a typical antihistaminic drug. The pharmacological receptors involved in these mepyramine-sensitive histamine responses have been defined as H-1 receptors (Ash, A. S. F & Schild H. O, Brit J Pharmacol Chem 1966, Vol 27, p 427). Histamine also stimulates the secretion of acid by the stomach (Loew E R & Chickering O, *Proc. Soc. Exp. Biol. Med.,* 1941, Vol. 48, p 65), increases the heart rate (Trendelenburg U *J. Pharmacol.* 1960, Vol. 130 p 450) and inhibits contractions in the rat uterus (Dews P B & Graham J D P, *Brit J. Pharmacol. Chem.,* 1946, Vol. 1, p 278); these actions cannot be antagonised by mepyramine and related drugs. In one embodiments, the H-2 antagonists useful in the oral care compositions or substances are those that blockade the receptors involved in mepyramine insensitive, non H-1 (H-2), histamine responses and do not blockade the receptors involved in mepyramine-sensitive histamine responses.

Selective H-2 antagonists are those compounds found to be H-2 antagonists through their performance in classical pre-clinical screening tests for H-2 antagonist function. Selective H-2 antagonists are identified as compounds which can be demonstrated to function as competitive or non-competitive inhibitors of histamine mediated effects in those screening models specifically dependent upon H-2 receptor function, but to lack significant histamine antagonist activity in those screening models dependent upon H-1 receptor function. Specifically, this includes compounds that would be classified as described by Black J W, Duncan W A M, Durant C J, Ganelline C R and Parsons E M, "Definitions and Antagonism of Histamine H2-Receptors", Nature 1972, vol 236 pp 385-390, as H-2 antagonists if assessed as described by Black through testing with the guinea pig spontaneously beating right atria in vitro assay and the rat gastric acid secretion in vivo assay, but shown to lack insignificant H-1 antagonist activity relative to H-2 antagonist activity, if assessed as described by Black with either the guinea pig ileum contraction in vitro assay or the rat stomach muscle contraction in vivo assay. In a preferred embodiments, selective H-2 antagonists demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are disclosed in U.S. Pat. Nos. 5,294,433 and 5,364,616 to Singer et al., issued Mar. 15, 1994 and Nov. 15, 1994 respectively and assigned to Procter & Gamble, wherein the selective H-2 antagonist is selected from the group consisting of cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728 and HB-408.4. Particularly preferred is cimetidien (SKF-92334), N-cyano-N'-methyl-N"-(2-(((5-methyl-1H-imidazol-4-yl)methyl)thio)ethyl)guanidine.

Cimetidine is also disclosed in the Merck Index, $11^{th}$ edition (1989), p. 354 (entry no 2279), and Physicians' Desk Reference, 46.sup.th edition (1992), p. 2228. Related preferred H-2 antagonists include burimamide and metiamide.

Analgesics

In some embodiments, anti-pain or desensitising agents can also be present in the oral care compositions or substances provided herein. Such agents may include, but are not limited to, strontium chloride, potassium nitrate, natural herbs such as gall nut, Asarum, Cubebin, Galanga, scutellaria, Liangmianzhen, Baizhi, etc. Analgesics also include the anti-inflammatory agents. Such agents may include, but are not limited to, non-steroidal anti-inflammatory agents of NSAIDs, such as ketorolac, flurbinprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx an effective amount of an NSAID.

Anti-Viral Agents

In some embodiments, provided herein are anti-viral actives. Anti-viral actives useful in the present composition include any known actives that are routinely used to treat viral infections. Such anti-viral actives are disclosed in Drug Facts and Comparisons (Loose leaf drug information service), Wolters Kluer Company, St. Louis, Mo., ©1997, pp. 402(a)-407(z), incorporated herein by reference in its entirety. Specific examples include anti-viral actives disclosed in U.S. Pat. No. 5,747,070 issued May 5, 1998 to Satyanarayana Majeti, incorporated herein by reference in its entirety. Said patent discloses the use of stannous salts to control viruses. Stannous salts and other anti-viral actives are described in detail in Kirk and Othmer, Encyclopedia of Chemical Technology, $3^{rd}$ Edition, vol. 23, Wiley Interscience Publishers (1982), pp. 42-71, incorporated herein by reference in its entirety. The stannous salts that may be used in the present embodiments would include organic stannous carboxylates and inorganic stannous halides. While stannous fluoride may be used, it is typically used only in combination with another stannous halide or one or more stannous carboxylates or another therapeutic agents.

Mucosally Absorbed Pharmacological Agents

In certain embodiments, provided herein are antitussives. Antitussives are actives particularly useful for arresting uncontrollable fits of coughing. Antitussives useful in the present embodiments include, but, are not restricted to, the group consisting of codeine, dextromethorphan, dextrorphan, diphenhydramine, hydrocodone, noscapine, oxycodone, pentoxyverine, pholcodine and mixtures thereof. Of these antitussives, dextromethorphan is preferred. Safe and effective amounts of other cough/cold drug actives may be included in such dextromethorphan-containing compositions. Particularly useful are the actives that are suited for absorption through the mucosal tissues as described in J. G. Hardman, The Pharmacologic Basis of Therapeutics, Ninth Edition, McGraw-Hill, New York, 1995. Other actives which are absorbed through the mucosal membrane include antihistamines; non-sedating antihistamines; decongestants; expectorants; mucolytics, analgesic, antipyretic anti-inflammatory agents, local anesthetics and mixtures thereof. As such these actives may also be incorporated into compositions provided herein.

Other Ingredients

In certain embodiments, these oral care products can contain a variety of nonessential optional components suitable for rendering such compositions more acceptable. Such conventional optional ingredients are well known to those skilled in the art e.g., preservatives such as benzyl alcohol, methyl paraben, propyl paraben and imidazolindinyl urea; cationic surfactants such as cetyl trimethylammonium chloride, lauryl trimethyl ammonium chloride, tricetyl methyl ammonium chloride and di(partially hydrogentated tallow) dimethylammonium chloride; thickeners and viscosity modifiers such as diethanolamide of long chain fatty acid (eg PEG 3 lauramide), block polymers of ethylene oxide and propylene oxide such as polyoxyalkylene ether of high molecular weight having water soluble, surface active, and wetting properties as is available under the trade name PLURONIC F88 (owned by BASF Corporation), sodium chloride, sodium sulphate, polyvinyl alcohol, and ethyl alcohol; pH adjusting agents and buffering agents such as citric acid, succinic acid, phosphoric acid, sodium hydroxide, sodium carbonate etc; sweetening agents; flavouring agents such as oil of peppermint, oil of *sassafras*, clove bud oil, peppermint, menthol, anethole, thymol, methylsalicylate, eucalyptol, *cassia*, 1-menthyl acetate, sage, eugenol, parsely oil, oxanone, oil of wintergreen, alpha-irisone, oil of spearmint, marjoram, lemon, orange, propenyl guaethol, cinnamon, and mixtures thereof; perfumes; dyes; and sequestering agents such as disodium ethylenediamine tetraacetate. Such agents are generally used individually at a level of from about 0.001% to about 10%, preferably from about 0.5% to about 5.0%, by weight, of the composition.

In certain embodiments, compositions for use herein may comprise less than about 10%, less than about 9%, less than about 8%, less than about 7%, less than about 6%, preferably less than about 5%, preferably less than about 4%, preferably less than about 3%, and more preferably less than about 2%, by weight, of volatile solvents. As defined herein volatile solvents refer to any material, organic or silicone in origin, which has a boiling point of about 200° C., or less, at one atmosphere pressure.

In certain embodiments, compositions provided herein are intended to be used without the need for curing, either hot curing or cold curing. As such it is intended that compositions provided herein are used alone and without any additional curing agent.

According to another aspect, the compositions provided herein have a viscosity of from about 1 Pa·s to about 1000 Pa·s. For all aspects provided herein, the compositions may have a viscosity of from about 2 Pa·s to about 500 Pa·s, preferably from about 5 Pa·s to about 300 Pa·s. In a preferred embodiments, the compositions provided herein may have a viscosity of from about 10 Pa·s to about 250 Pa·s.

Rheology Modifiers

In certain embodiments, compositions provided herein can optionally comprise a rheology modifier which inhibits settling and separation of components or control settling in a manner which facilitates re-dispersion and may control rheological flow properties. Suitable rheology modifiers herein include organo modified clays, silicas, cellulose polymers such as hydroxypropylmethyl cellulose, xanthan gum, carbomers, inorganic clay polymers, polycarboxylates, EO/PO block copolymers (poloxamers) thickening silicas and mixtures thereof. In certain embodiments, preferred organophilic clays comprise Quaternium-18 hectorite or Stearalkonium hectorite, such as those commercially available under the trade names BENTONE 27 and 38 from Rheox, organoclay dispersion such as a specially prepared dispersion of a non-animal origin organically modified hectorite in isododecane including that commercially available under the trade name BENTONE GEL ISD (owned by Elementis Specialties, Inc. of Windsor, N.J.); or bentonites organo modified clays such as those commercially available under the trade names BENTONE 34 from Rheox or the CLAYTONE Series from Southern Clay Products; and mixtures thereof. In some embodiments, preferred silicas may be fumed silica such as those commercially available under the trade name AEROSIL series from Degussa or the CAB-O-SIL series from Cabot Corporation, silica gels such as the SYLODENT or SYLOX series from W R Grace & Co or precipitated silica such as ZEOTHIX 265 from J. M. Huber Corporation. In some embodiments, a rheology modifier is preferably present in the composition at a level of from about 0.1% to about 15%, preferably from about 0.5% to about 10%, and even more preferably from about 1% to about 3%, by weight, of the composition.

Coated Oral Devices

In some embodiments, provided herein are methods comprising attaching boundary lubricant molecules to the surface of oral/dental devices and using supplementation to replenish boundary lubrication over the course of wear; for instance, the supplementation of hyaluronic acid and/or PRG4 in the presence of a PRG4-coated oral device. Without limitation, such oral/dental devices include braces, retainers, mandibular advancement devices, mouth guards, and mouthpieces.

In one embodiment, attachment of molecules to the surface of the oral devices can be achieved through common linker chemistries, such as homo- and heterobifunctional linkers such as N-hydroxy succinimidyl esters, biotin, avidin, streptavidin, maleimides, thiol bonds, amine chemistries, hydrazones, and the like. In yet another embodiment attachment is achieved through adsorption As used herein, the term "PRG4", "PRG4 protein" or "proteoglycan 4" protein, is used interchangeably with the term "lubricin" protein. PRG4 is used herein also to encompass the term megakaryocyte stimulating factor (MSF), that has been accepted for the UCL/HGNC/HUGO Human Gene Nomenclature data base, and superficial zone protein (SZP). The PRG4 or lubricin protein (used interchangeably herein with lubricin proteoglycan) as used herein refers to any isolated or purified native or recombinant lubricin proteins, homologs, functional fragments or motifs, isoforms, and/or mutants thereof. In certain embodiments, the isolated or purified PRG4 protein comprises an amino acid sequence for a human native or recombinant lubricin protein. In other embodiments, the isolated or purified PRG4 protein comprises an amino acid sequence encoded by prg4 gene exons that encode the full length PRG4 protein or isoforms' primary structures. The proteoglycan 4 (prg4) gene contains 12 exons. The PRG4 protein used herein comprises an amino acid sequence encoded by prg4 gene exons 1-12, more preferably, exons 6-12, and most preferably, exons 9-12. The MSF (PRG4) exon boundaries are provided in Table 1.

TABLE 1

MSF Exon Boundaries

| Exon | Amino acid sequence in SEQ ID NO: 1 |
|---|---|
| 1 | 1-24, inclusive |
| 2 | 25-66, inclusive |
| 3 | 67-104, inclusive |
| 4 | 105-155, inclusive |
| 5 | 156-199, inclusive |
| 6 | 200-1140, inclusive |
| 7 | 1141-1167, inclusive |
| 8 | 1168-1212, inclusive |
| 9 | 1213-1263, inclusive |
| 10 | 1264-1331, inclusive |
| 11 | 1332-1371, inclusive |
| 12 | 1372-1404, inclusive |

As used herein, the PRG4 protein includes any PRG4 proteins now known, or later described. In certain embodiments, a preferred PRG4 protein amino acid sequence is provided in SEQ ID NO: 1. In certain embodiments, the PRG4 protein lacks the amino acid sequence of residues 1-24, inclusive, of SEQ ID NO:1. The PRG4 protein shares the primary amino acid structure of any known PRG4 proteins or isoforms with at least 60% homology, preferably 75% homology, more preferably 85%, 90%, 91%, 92%, 93%, 94%, 95%, 96%, 97%, 98%, 99% or more homology. In certain embodiments, a preferred PRG4 protein has an average molar mass of between 50 kDa and 25 kDa, comprising one or more biological active portions of the PRG4 protein, or functional fragments, such as a lubricating fragment, or a homolog thereof.

As used herein, the PRG4 protein comprises a biological active portion of the protein. As used herein, a "biologically active portion" of the PRG4 protein includes a functional fragment of a protein comprising amino acid sequences sufficiently homologous to, or derived from, the amino acid sequence of the protein, which includes fewer amino acids than the full length protein, and exhibits at least one activity of the full-length protein. Typically a biologically active portion comprises a functional domain or motif with at least one activity of the protein. A biologically active portion of a protein can be a polypeptide which is, for example, 10, 25, 50, 100, 200, or more amino acids in length. In one embodiment, a biologically active portion of the PRG4 protein can be used as a therapeutic agent alone or in combination with other therapeutic agents for treating undesirable or decreased articular cartilage boundary lubrication.

In yet another embodiment, functional fragments, multimers (e.g., dimers, trimers, tetramers, etc.), homo logs or orthologs of PRG4 are used in an oral care composition provided herein. Functional fragments and homo logs of PRG4 include those with fewer repeats within the central mucin-like KEPAPTT-repeat domain (SEQ ID NO:2), glycosylated and non-glycosylated forms of the protein, splice variants, recombinant forms, and the like. A lubricating fragment of PRG4 exhibits at least 20%, 30%, 40%, 50%, 60%, 70%, 80%, 90%, or 95% of the lubricating effect of human PRG4, as measured qualitatively, mechanically, optically, electrically, or by biochemical assay.

The nucleic acid and amino acid sequences of several native and recombinant PRG4 or lubricin proteins, and characterization of the PRG4 proteins and various isoforms are disclosed in, for instance, U.S. Pat. Nos. 5,326,558; 6,433,142; 7,030,223; 7,361,738 to Turner et al., and U.S. Pat. Nos. 6,743,774 and 6,960,562 to Jay et al., U.S. Publication No. 20070191268 to Flannery et al. also discloses recombinant PRG4 or lubricin molecules useful in the present embodiments.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and further transformed and expressed in a host cell for producing recombinant PRG4 protein.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising an active domain of the PRG4 gene and a nucleic acid sequence amplified using a primer provided herein.

In certain embodiments, the PRG4 protein encoding nucleic acid may contain one or more mutations, deletions, or insertions. In such embodiments, the PRG4 protein encoding nucleic acid is at least 60% homology, preferably 75% homology, more preferably 85%, 90%, 91%, 92%, 93%, 94%, 95%, 96%, 97%, 98%, 99%, or more homology, to a wild type PRG4 protein encoding nucleic acid.

As used herein, the term "'cDNAs" includes DNA that is complementary to mRNA molecules present in a cell or organism mRNA that can be convertned into cDNA with an enzyme such as reverse transcriptase. In certain embodiments, the cDNA encoding PRG4 protein is isolated from PRG4 mRNA expressed in human corneal or conjunctival epithelial cells using an RT-PCR method well known in the art.

As used herein, the terms "polynucleotide," "nucleic acid/nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment provided herein that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of thymine when the polynucleotide is RNA, instead of DNA. This alphabetical representation can be inputted into databases in a computer and used for bioinformatics applications such as, for example, functional genomics and homology searching.

As used herein, the term "isolated polynucleotide/cDNA" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule encoding the PRG4 protein used in the present embodiments can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material, or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art. As used herein, a "native or naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In certain embodiments, the PRG4 protein used herein refers to PRG4 proteins or various homologs or isoforms thereof that are naturally or recombinantly expressed in humans or other host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. The term "genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" can be any cells that express a human PRG4 protein.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the PRG4 protein (e.g., SEQ ID NO:1).

As used herein, the term "orthologs" refers to two nucleic acids from different species, but that have evolved from a common ancestral gene by speciation. Normally, orthologs encode peptides having the same or similar functions. In some embodiments, orthologs provided herein will generally exhibit at least 80-85%, more preferably 85-90% or 90-95%, and most preferably 95%, 96%, 97%, 98%, or even 99% identity, or 100% sequence identity, with all or part of the amino acid sequence of any known PRG4 proteins (e.g., SEQ ID NO:1), isoforms, or analogs thereof, and will exhibit a function similar to these peptides. As also used herein, the term "paralogs" refers to two nucleic acids that are related by duplication within a genome. Paralogs usually have different functions, but these functions may be related.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). Preferably, the isolated amino acid homologs included in the present embodiments are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of any known PRG4 protein (e.g., SEQ ID NO:1).

In certain embodiments, an isolated nucleic acid homolog encoding the PRG4 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such PRG4 protein (e.g., SEQ ID NO:1).

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Furthermore, the PRG4 protein used herein includes PRG4 protein encoded by a polynucleotide that hybridizes to the polynucleotide encoding PRG4 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. In certain embodiments, provided herein are polynucleotides capable of hybridizing under reduced stringency conditions, more preferably stringent conditions, and most preferably highly stringent conditions, to polynucleotides encoding PRG4 protein described herein. As used herein, the term "stringent conditions" refers to hybridization overnight at 60° C. in 10× Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10× Denhart's solution, 6×SSC, 0.5% SDS and 100 mg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are well known in the art. Accordingly, the PRG4 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human PRG4 protein (e.g., SEQ ID NO:1) or a specific isoform or homolog thereof.

In some embodiments, the PRG4 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In certain embodiments, the chimeric protein is a chimera of PRG4 protein with other PRG4 protein isoforms.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In certain embodiments, the language "substantially free of cellular material" includes preparations of a PRG4 protein having less than about 30% (by dry weight) of other proteins (also referred to herein as a "contaminating protein"), more preferably less than about 20%, still more preferably less than about 10%, and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

The term "oral care active" as used herein refers to any composition which has a prophylactic, therapeutic or cosmetic benefit either directly within the oral cavity or which is absorbed via the oral cavity but which has its primary benefit elsewhere. The term "treatment" as used herein refers to process of applying a substance to the oral cavity, wherein that substance may or may not comprise an oral care active, such that a prophylactic, therapeutic or cosmetic benefit is achieved.

The term "oral cavity" as referred to herein refers to the cavity from the lips to the epiglotis. The "hard tissues" comprise tissues such as the teeth and peridontal support and the like and the "soft tissues" comprise tissues such as the gums, the tongue, the surfaces of the buccal cavity and the like. Within the scope of this application the hard and soft tissues of the oral cavity should also be considered to comprise any devices which are used therein for example dentures, partial dentures, braces and the like.

In certain embodiments, the subjects treated by the present compositions and methods include mammalian subjects, including, human, monkey, ape, dog, cat, cow, horse, goat, pig, rabbit, mouse and rat.

Throughout this application, various publications are referenced. The disclosures of all of these publications and those references cited within those publications in their entireties are hereby incorporated by reference into this application.

It should also be understood that the foregoing relates to preferred embodiments and that numerous changes may be made therein without departing from the present scope. The invention is further illustrated by the following examples, which are not to be construed in any way as imposing limitations upon the scope thereof. On the contrary, other embodiments, modifications, and equivalents thereof, which, after reading the description herein, may suggest themselves to those skilled in the art without departing from the spirit of the present embodiments and/or the scope of the appended claims.

Other features and advantages provided herein will be apparent from the following description of the preferred embodiments thereof and from the claims.

In certain embodiments, the therapeutically active concentration of PRG4 can range from 1 µg/mL to 1 mg/mL. In other embodiments, the therapeutically active concentration of PRG4 can range from 20 µg/mL to 300 µg/mL. These orally acceptable compositions can be in the form of a solution (i.e., mouthwash), a lyophilized powder, a gel that is topically applied to the hard or soft tissues of the mouth, encapsulated protein that is slow-released into the oral cavity, or other delivery mechanisms that increase the concentration of PRG4 or PRG4 inducer local to the tissue of interest. Gels, sols, solutions, or encapsulated compositions could also be used in conjunction with oral delivery devices such as molded trays, aerosol sprays, dissolvable tabs (e.g., those used in oral care and breath freshening dissolving strips including those available under the commercial trade name LISTERINE POCKETPAKS owned by Johnson & Johnson Corporation of New Brunswick, N.J.), non-dissolvable whitening strips, toothbrush coatings, chewing gum, and so forth.

Because the activity of PRG4 is meant to be long lasting, the current embodiments also allow for methods of treatment following routine dental hygiene or dental surgery that may strip the endogenous pellicle layer or glycocalyx from the oral cavity. In one preferred embodiment, provided herein is a method of applying a gel containing a 300 µg/mL PRG4 to a molded tray, comprising having the patient bite down on the tray and holding their mouth shut for a few minutes while the PRG4 binds to the enamel. In another preferred embodiment, during home use, a person adheres a whitening strip to their upper and lower teeth, wherein the whitening strip delivers a carbamide peroxide/PRG4 gel to the enamel surface. In yet other embodiments, a user would purchase a two-step whitening strip kit that contains standard whitening strips for the first step, followed by a PRG4 strip, gel, or spray to protect the enamel following a peroxide bleaching.

As the combination of PRG4 with certain oral care ingredients may compromise its function when used simultaneously, provided herein are methods of encapsulating PRG4 in dissolvable delivery devices such as tortuous path microspheres, nanoparticles, emlusifications, and so forth.

In certain embodiments, PRG4 protein is secreted into saliva and spontaneously binds to the hard and soft tissues of the oral cavity. Whether due to disease (i.e., Sjögren's Syndrome, periodontal disease, diabetes), iatrogenic factors (chemotherapy), aging, hormone deficiency, or other factors, the replenishment of endogenous PRG4 confer lubricating and anti-adhesive (and therefore, by extension, anti-bacterial) activity to the oral cavity. In certain embodiments, provided herein are orally acceptable compositions that include a therapeutic concentration of PRG4 protein. In other embodiments, provided herein are orally acceptable compositions that include a PRG4 inducer, such as an androgen, selective androgen receptor modulator, TGF-β, etc.

SEQUENCE LIST

SEQ ID NO: 1
MAWKTLPIYLLLLLSVFVIQQVSSQDLSSCAGRCGEGYSRDATCNCDYNCQHYMECCPD
FKRVCTAELSCKGRCFESFERGRECDCDAQCKKYDKCCPDYESFCAEVHNPTSPPSSKK
APPPSGASQTIKSTTKRSPKPPNKKKTKKVIESEEITEEHSVSENQESSSSSSSSSSSTIRKI
KSSKNSAANRELQKKLKVKDNKKNRTKKKPTPKPPVVDEAGSGLDNGDFKVTTPDTST
TQHNKVSTSPKITTAKPINPRPSLPPNSDTSKETSLTVNKETTVETKETTTTNKQTSTDGKE
KTTSAKETQSIEKTSAKDLAPTSKVLAKPTPKAETTTKGPALTTPKEPTPTTPKEPASTTPK
EPTPTTIKSAPTTPKEPAPTTTKSAPTTPKEPAPTTTKEPAPTTPKEPAPTTTKEPAPTTTKS
APTTPKEPAPTTPKKPAPTTPKEPAPTTPKEPTPTTPKEPAPTTKEPAPTTPKEPAPTAPKKP
APTTPKEPAPTTPKEPAPTTTKEPSPTTPKEPAPTTTKSAPTTTKEPAPTTTKSAPTTPKEPS
PTTTKEPAPTTPKEPAPTTPKKPAPTTPKEPAPTTPKEPAPTTTKKPAPTTPKEPAPTTPKET
APTTPKKLTPTTPEKLAPTTPEKPAPTTPEELAPTTPEEPTPTTPEEPAPTTPKAAAPNTPKE
PAPTTPKEPAPTTPKEPAPTTPKETAPTTPKGTAPTTLKEPAPTTPKKPAPKELAPTTTKEP
TSTTCDKPAPTTPKGTAPTTPKEPAPTTPKEPAPTTPKGTAPTTLKEPAPTTPKKPAPKELA
PTTTKGPTSTTSDKPAPTTPKETAPTTPKEPAPTTPKKPAPTTPETPPPTTSEVSTPTTTKEP
TTIHKSPDESTPELSAEPTPKALENSPKEPGVPTTKTPAATKPEMTTTAKDKTTERDLRTT
PETTTAAPKMTKETATTTEKTTESKITATTTQVTSTTTQDTTPFKITTLKTTTLAPKVTTTK
KTITTTEIMNKPEETAKPKDRATNSKATTPKPQKPTKAPKKPTSTKKPKTMPRVRKPKTT
PTPRKMTSTMPELNPTSRIAEAMLQTTTRPNQTPNSKLVEVNPKSEDAGGAEGETPHMLL
RPHVFMPEVTPDMDYLPRVPNQGIIINPMLSDETNICNGKPVDGLTTLRNGTLVAFRGHY
FWMLSPFSPPSPARRITEVWGIPSPIDTVFTRCNCEGKTFFFKDSQYWRFTNDIKDAGYPK
PIFKGFGGLTGQIVAALSTAKYKNWPESVYFFKRGGSIQQYIYKQEPVQKCPGRRPALNY
PVYGETTQVRRRRFERAIGPSQTHTIRIQYSPARLAYQDKGVLHNEVKVSILWRGLPNVV
TSAISLPNIRKPDGYDYYAFSKDQYYNIDVPSRTARAITTRSGQTLSKVWYNCP

SEQ ID NO: 2:
KEPAPTT

-continued

| SEQUENCE LIST |
|---|

SEQ ID NO: 3:
GATGCAGGGTACCCCAAA (human, sense)

SEQ ID NO: 4:
CAGACTTTGGATAAGGTCTGCC (human, antisense)

What is claimed is:

1. A method for treating an individual having a dental disease or condition selected from the group consisting of dental caries, tooth discoloration, periodontal disease, and pellicle layer reduction, the method comprising administering to an oral cavity of said individual a composition comprising a proteoglycan 4 (PRG4) protein comprising the amino acid sequence of SEQ ID NO:1 less amino acid residues 1-24, wherein said composition is administered in a therapeutically effective amount sufficient to treat said disease or condition.

2. The method of claim 1, wherein the disease or condition is periodontal disease.

3. The method of claim 1, wherein said PRG4 protein is suspended in an orally acceptable solution.

4. The method of claim 1, wherein the administering to the oral cavity of said individual is by topical application to one or more teeth of the individual.

5. The method of claim 1, wherein the administering to the oral cavity of said individual is by topical application to a soft tissue of the oral cavity.

6. The method of claim 5, wherein the soft tissue is the gums.

7. The method of claim 1, wherein the administering to the oral cavity of said individual is by a mouth wash or rinse solution.

8. The method of claim 1, wherein the administering to the oral cavity of said individual is by a gel, a powder, a spray, a chewing gum, or a dissolvable tablet.

9. The method of claim 1, wherein the effective amount is between 10 µg/mL and 10,000 µg/mL.

10. The method of claim 1, wherein the effective amount is between 50 µg/mL and 5,000 µg/mL.

11. The method of claim 1, wherein the effective amount is between 100 µg/mL and 300 µg/mL.

12. The method of claim 1, wherein the PRG4 protein has an average molar mass between 50 kDa and 400 kDa.

13. The method of claim 1, wherein the composition further comprises an oral care active selected from the group consisting of teeth color modifying substances, anti-tartar agents, anti-plaque agents, fluoride ion sources, anti-microbial agents, peroxides, polyphosphates, xylitol, triclosan, stannous fluoride, soluble zinc salts, potassium nitrate, and mixtures thereof.

14. The method of claim 13, wherein the composition comprises from about 0.01% to about 20% by weight of the oral care active.

15. The method of claim 1, wherein the composition further comprises a surface active phospholipid.

16. The method of claim 15, wherein the surface active phospholipid is selected from the group consisting of L-α-dipalmitoylphosphatidylcholine, phosphatidylcholine, phosphatidylethanolamine, and sphingomyelin.

17. The method of claim 1, wherein the composition further comprises an effective amount of sodium hyaluronate or hyaluronic acid.

* * * * *